(12) United States Patent
Mou et al.

(10) Patent No.: US 9,579,276 B2
(45) Date of Patent: Feb. 28, 2017

(54) CLEAR SUNSCREEN COMPOSITION FOR APPLICATION ONTO WET OR DRY SKIN

(71) Applicant: L'OREAL, Paris (FR)

(72) Inventors: Tsung-Hui Marisal Mou, Towaco, NJ (US); Paula Cziryak, Eatontown, NJ (US); Anthony Potin, Hoboken, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/104,029

(22) Filed: Dec. 12, 2013

(65) Prior Publication Data

US 2015/0164773 A1   Jun. 18, 2015

(51) Int. Cl.
*A61K 8/88* (2006.01)
*A61Q 17/04* (2006.01)
*A61K 8/81* (2006.01)
*A61K 8/89* (2006.01)

(52) U.S. Cl.
CPC ............... *A61K 8/88* (2013.01); *A61K 8/8147* (2013.01); *A61K 8/8152* (2013.01); *A61K 8/89* (2013.01); *A61Q 17/04* (2013.01); *A61K 2800/262* (2013.01)

(58) Field of Classification Search
None
See application file for complete search history.

(56) References Cited

U.S. PATENT DOCUMENTS

| | | | |
|---|---|---|---|
| 2,463,264 A | 3/1949 | Graenacher et al. | |
| 4,077,441 A | 3/1978 | Rosen et al. | |
| 4,850,517 A | 7/1989 | Ter Stege | |
| 5,061,481 A | 10/1991 | Suzuki et al. | |
| 5,166,355 A | 11/1992 | Leistner et al. | |
| 5,219,560 A | 6/1993 | Suzuki et al. | |
| 5,237,071 A | 8/1993 | Leistner et al. | |
| 5,412,004 A | 5/1995 | Tachibana et al. | |
| 5,624,663 A | 4/1997 | DeFlandre et al. | |
| 5,811,487 A | 9/1998 | Schulz, Jr. et al. | |
| 6,191,301 B1 | 2/2001 | Habeck et al. | |
| 6,225,467 B1 | 5/2001 | Esteghamatian et al. | |
| 6,630,133 B1* | 10/2003 | Dupuis | 424/70.1 |
| 8,236,284 B1 | 8/2012 | Perez et al. | |
| 2007/0178057 A1* | 8/2007 | SenGupta | A61K 8/0208 424/59 |
| 2012/0058192 A1* | 3/2012 | Singleton | A61K 8/062 424/493 |
| 2015/0093343 A1* | 4/2015 | Bonda | A61Q 19/00 424/60 |

FOREIGN PATENT DOCUMENTS

| | | | |
|---|---|---|---|
| BR | WO 2012012857 A2 * | 2/2012 | ............ A61K 8/062 |
| DE | 19726184 A1 | 12/1998 | |
| DE | 19746654 A1 | 2/1999 | |
| DE | 19755649 A1 | 6/1999 | |
| DE | 19855649 A1 | 6/2000 | |
| DE | 10162844 A1 | 7/2003 | |
| EP | 518773 A1 | 12/1992 | |
| EP | 669323 A1 | 2/1995 | |
| EP | 705593 A1 | 4/1996 | |
| EP | 832642 A1 | 4/1998 | |
| EP | 893119 A1 | 1/1999 | |
| EP | 967200 A1 | 12/1999 | |
| EP | 1008586 A1 | 6/2000 | |
| EP | 1027883 A1 | 8/2000 | |
| EP | 1133980 A2 | 9/2001 | |
| EP | 1133981 A2 | 9/2001 | |
| EP | 1300137 A2 | 4/2003 | |
| GB | 2303549 A | 2/1997 | |
| JP | 2295912 A | 6/1990 | |
| WO | 93/04665 A1 | 3/1993 | |
| WO | WO 98/07404 * | 5/1998 | |
| WO | 2004/006878 A1 | 1/2004 | |
| WO | 2004/085412 A2 | 10/2004 | |
| WO | 2005/058269 A1 | 6/2005 | |
| WO | 2006/032741 A1 | 3/2006 | |
| WO | 2006/034982 A1 | 4/2006 | |
| WO | 2006/034985 A1 | 4/2006 | |
| WO | 2006/034991 A1 | 4/2006 | |
| WO | 2006/034992 A1 | 4/2006 | |
| WO | 2006/035000 A1 | 4/2006 | |
| WO | 2006/035007 A1 | 4/2006 | |
| WO | WO 2012/059348 * | 5/2012 | |
| WO | WO 2012/149355 * | 11/2012 | |

OTHER PUBLICATIONS

Lubrizol technical data sheet "Pemulen™ TR-1 and TR-2 Polymeric Emulsifiers," Jul. 22, 2009;.*
Marco "Consumer Reports: why are companies lying about putting nanoparticles in your sunscreen?" posted online Oct. 31, 2008; http://consumerist.com/2008/10/31/consumer-reports-why-are-companies-lying-about-putting-nanoparticles-in-yoursunscreen/.*

* cited by examiner

*Primary Examiner* — David J Blanchard
*Assistant Examiner* — Alissa Prosser
(74) *Attorney, Agent, or Firm* — McNees Wallace & Nurick LLC

(57) ABSTRACT

The present invention is directed to a composition containing: at least one cross-linked copolymers of acrylic acid and a hydrophobic co-monomer; at least one neutralized polyacrylic acid; at least one silicone acrylate; oil; water; and at least one sunscreen active, wherein the composition is initially clear in appearance and remains clear in appearance upon application onto wet skin.

15 Claims, No Drawings

CLEAR SUNSCREEN COMPOSITION FOR APPLICATION ONTO WET OR DRY SKIN

BACKGROUND OF THE INVENTION

Conventional sunscreen products generally take the form of ultraviolet (UV)-filter compounds and/or particulate UV-screening compounds (collectively, "sunscreen actives") that are solublized, emulsified, or dispersed in a vehicle, which is topically applied to the skin. The sunscreen actives, typically through the aid of polymers and other ingredients included in the vehicle, form a thin, protective, and often water-resistant layer on the skin.

While certain products are successful at providing a durable protective barrier when applied to dry skin, such is not typically the result when applied to skin that is damp with sweat or has residual water thereon. In fact, when applied to wet skin, the tendency of conventional sunscreen products is to dilute the sunscreen actives, smear, and form an incomplete film, often one that flakes or peels off the skin, and/or takes on a pasty, white appearance. The end result is unattractive, and renders the skin with poor protection from the sun's rays.

Others have contemplated a solution to this problem by using a water-in-oil emulsifier to "self-emulsify," presumably in the presence of residual water present on the skin. However, the applicants have recognized that severe aesthetic and performance problems still exist in most all "wet skin" sunscreen products. Accordingly, the applicants have now identified a novel sunscreen composition that is suitable for use on wet skin and resists the tendency to whiten in the presence of residual water.

BRIEF SUMMARY OF THE INVENTION

The present invention is directed to a composition containing:
(a) at least one cross-linked copolymers of acrylic acid and a hydrophobic co-monomer;
(b) at least one neutralized polyacrylic acid;
(c) at least one silicone acrylate;
(d) oil;
(e) water; and
(f) at least one sunscreen active
wherein the composition is initially clear in appearance and remains clear in appearance upon application onto wet skin.

DETAILED DESCRIPTION OF THE INVENTION

Other than in the operating examples, or where otherwise indicated, all numbers expressing quantities of ingredients and/or reaction conditions are to be understood as being modified in all instances by the term "about".

As used herein, the expression "at least one" means one or more and thus includes individual components as well as mixtures/combinations.

"Cosmetically acceptable" means that the item in question is compatible with any keratinous substrate. For example, "cosmetically acceptable carrier" means a carrier that is compatible with any keratinous substrate.

A "physiologically acceptable medium" means a medium which is not toxic and can be applied to the skin, lips, hair, scalp, lashes, brows, nails or any other cutaneous region of the body. The composition of the instant disclosure may especially constitute a cosmetic or dermatological composition.

The inventors have surprisingly discovered that the association of a carboxyvinyl polymer, a neutralized polyacrylic acid, a silicone acrylate, oil, water and sunscreen active yields an initially clear composition which, when applied onto a wet keratinous substrate such as skin, hair or nails, maintains its clear appearance evidencing stability of the composition, i.e. it does not become cloudy when applied onto wet skin which would indicate a "lack" of stability.

The term "clear" as used herein means a semi-translucent, off-white to non-white, glossy, luminous, fluid lotion.

Cross-Linked Copolymers of Acrylic Acid and Hydrophobic Co-Monomer

Suitable carboxyvinyl polymers for use in the present invention include, but are not limited to, those having a network of cross-linked polymer chains. The polymers are characterized as having carboxylic acid functional groups and preferably contain from 2 to 7 carbon atoms per functional group. Prior to cross-linking, the carboxyvinyl polymer useful in the present invention typically has a molecular weight of at least about 50,000, more typically at least about 200,000 and still more typically at least about 400,000 atomic mass units (amu). That molecular weight is typically less than about 6 million, more typically less than about 1 million and still more typically less than about 600,000 amu.

Preferred carbomers or carboxyvinyl polymers are formed of acrylic acid cross-linked with polyalkenyl ethers or divinyl glycol. The polymers are typically polymerized in a solvent such as benzene or ethyl acetate. Ethyl acetate is generally preferred for the present invention since solvent residue can remain with the polymers and ethyl acetate tends to be more biocompatible and/or can have a relatively lower degree of toxicity relative to some other solvents. The carbomers or carboxyvinyl polymers can be cross-linked with allyl sucrose or allyl penta erythritol.

Preferred carboxyvinyl polymers include water-soluble and water-swellable carbomers, available under the trade name CARBOPOL® from the B.F. Goodrich Company. The commercially available polymers Carbopol® 934P, 940, 974P and 980 are highly preferred. A particularly preferred carboxyvinyl polymer is an acrylate/C10-C30 aklylacrylate copolymer commercially available from Lubrizol under the tradename PEMULEN®.

The amount of cross-linked copolymer of acrylic acid and hydrophobic co-monomer present in the composition of the present invention is typically from about 0.01 to 0.5%, more preferably from about 0.01 to 0.4%, and most preferably from about 0.01 to 0.3% by weight, all weights based on the total active weight of the composition.

Neutralized Polyacrylic Acids

Suitable neutralized polyacrylic acids for use in the present invention include, but are not limited to, salts of polyacrylic acid. These are anionic polyelectrolytes with negatively charged carboxylic groups in the main chain. Examples thereof include the sodium, potassium, lithium and ammonium neutralized salts of polyacrylic acid. The most preferred neutralized polyacrylic acid is sodium polyacrylate.

The amount of neutralized polyacrylic acid polymer present in the composition of the present invention is typically from about 0.01 to 2%, more preferably from about 0.01 to 1%, and most preferably from about 0.01 to 0.75% by weight, all weights based on the total active weight of the composition.

Silicone Acrylates

A composition used according to the invention also contains at least one copolymer comprising carboxylate groups and polydimethylsiloxane groups.

In the present patent application, the expression "copolymer comprising carboxylate groups and polydimethylsiloxane groups" means a copolymer obtained from (a) one or more carboxylic (acid or ester) monomers, and (b) one or more polydimethylsiloxane (PDMS) chains.

In the present patent application, the term "carboxylic monomer" means both carboxylic acid monomers and carboxylic acid ester monomers. Thus, the monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconate and/or crotonate. According to one preferred embodiment of the invention, the monomers in ester form are more particularly chosen from linear or branched, preferably $C_1$-$C_{24}$ and better still $C_1$-$C_{22}$ alkyl acrylates and methacrylates, the alkyl radical preferably being chosen from methyl, ethyl, stearyl, butyl and 2-ethylhexyl radicals, and mixtures thereof.

Thus, according to one particular embodiment of the invention, the copolymer comprises as carboxylate groups at least one group chosen from acrylic acid and methacrylic acid, and methyl, ethyl, stearyl, butyl or 2-ethylhexyl acrylate or methacrylate, and mixtures thereof.

In the present patent application, the term "polydimethylsiloxanes" (also known as organopolysiloxanes and abbreviated as PDMS) denotes, in accordance with what is generally accepted, any organosilicon polymer or oligomer of linear structure, of variable molecular weight, obtained by polymerization and/or polycondensation of suitably functionalized silanes, and consisting essentially of a repetition of main units in which the silicon atoms are linked together via oxygen atoms (siloxane bond $\equiv$Si—O—Si$\equiv$), comprising trimethyl radicals directly linked via a carbon atom to the said silicon atoms. The PDMS chains that may be used to obtain the copolymer used according to the invention comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The radical-polymerizable group may especially be an acrylic or methacrylic group, in particular a group $CH_2$=$CR_1$—CO—O—$R_2$, in which $R_1$ represents a hydrogen or a methyl group, and $R_2$ represents —$CH_2$—, —$(CH_2)_n$— with n=3, 5, 8 or 10, —$CH_2$—$CH(CH_3)$—$CH_2$—, —$CH_2$—$CH_2$—O—$CH_2$—$CH_2$—, —$CH_2$—$CH_2$—O—$CH_2$—$CH_2$—CH($CH_3$)—$CH_2$— or —$CH_2$—$CH_2$—O—$CH_2CH_2$—O—$CH_2$—$CH_2$—$CH_2$—.

The copolymers used in the composition of the invention are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer, as described, for example, in documents U.S. Pat. No. 5,061,481 and U.S. Pat. No. 5,219,560.

The copolymers obtained generally have a molecular weight ranging from about 3000 to 200 000 and preferably from about 5000 to 100 000.

The copolymer used in the composition of the invention may be in its native form or in dispersed form in a solvent such as lower alcohols containing from 2 to 8 carbon atoms, for instance isopropyl alcohol, or oils, for instance volatile silicone oils (for example cyclopentasiloxane).

As copolymers that may be used in the composition of the invention, mention may be made, for example, of copolymers of acrylic acid and of stearyl acrylate containing polydimethylsiloxane grafts, copolymers of stearyl methacrylate containing polydimethylsiloxane grafts, copolymers of acrylic acid and of stearyl methacrylate containing polydimethylsiloxane grafts, copolymers of methyl methacrylate, butyl methacrylate, 2-ethylhexyl acrylate and stearyl methacrylate containing polydimethylsiloxane grafts. As copolymers used in the composition of the invention, mention may be made in particular of the copolymers (INCI name: acrylates/dimethicone copolymer) sold by the company Shin-Etsu under the tradenames KP-561 in which the polymer is not dispersed in solvent, KP-541 in which the copolymer is dispersed in isopropyl alcohol, KP-545 in which the copolymer is dispersed in cyclopentasiloxane, and KP-550 in which the copolymer is dispersed in isododecane.

A particularly preferred silicone acrylate is a graft copolymer having an acrylic acid polymer backbone and polydimethylsiloxane side chains, commercially available from Shin Etsu under the tradenames KSP545 and KSP545L.

The amount of silicone acrylate present in the composition of the present invention is typically from about 0.05 to 20%, more preferably from about 0.05 to 10%, and most preferably from about 0.05 to 5% by weight, all weights based on the total active weight of the composition.

Oils

Examples of oils that may be included in the sunscreen compositions include: hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol® 810, 812 and 818 by the company Dynamit Nobel, jojoba oil, shea butter oil and caprylyl glycol; synthetic esters and ethers, especially of fatty acids, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew® SL 205 by the company Ajinomoto; linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam oil, or the mixture of n-undecane ($C_{11}$) and of n-tridecane ($C_{13}$) sold under the reference Cetiol® UT by the company Cognis; fluoro oils that are partially hydrocarbon-based and/or silicone-based, for instance those described in document JP-A-2 295 912; silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxy-diphenylsiloxanes, diphenyl dimethicones, diphenylmethyl-diphenyltrisiloxanes or 2-phenylethyl trimethylsiloxy silicates, and polymethylphenylsiloxanes; mixtures thereof.

Additional examples include benzoic acid esters of $C_9$-$C_{15}$ alcohols, isononyl iso-nonanoate, $C_{12}$-$C_{15}$ alkyl benzoate, or any combinations thereof.

Specific examples of oils include cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of $C_9$-$C_{15}$ alcohols, isononyl iso-nonanoate, alkanes, mineral oil, silicone, dimethyl polysiloxane, ether, polyoxypropylene butyl ether, polyoxypropylene cetyl ether, $C_{12}$-$C_{15}$ alkyl benzoate, aryl alkyl benzoate, Isopropyl Lauroyl sarcosinate, and any combinations thereof.

Examples of hydrophilic organic solvents that may be included in the sunscreen compositions include: monohydric $C_1$-$C_8$ alcohols such as ethanol, propanol, butanol, isopropanol, isobutanol; Polyethylene glycols from 6 to 80 ethylene oxides such as propylene glycol, isoprene glycol, butylene glycol, glycerol, sorbitol; mono or di-alkyl isosorbides such as dimethyl isosorbide;

Examples of amphiphilic organic solvents include: polypropylene glycol (PPG) like propylene glycol alkyl ester or alkyl ether of PPG like PPG-23 oleyl ether and PPG-36 oleate.

The above lists are only examples and not limiting.

The total amount of oils present in the composition is typically from about 0.1, 0.5, 1.0, or 2.5 wt. % to about 5.0, 7.5, 10.0, 15.0, 20.0, 30.0, or 40.0 wt. %, based on the total active weight of the composition.

Emulsifiers

The sunscreen compositions typically include at least one emulsifier such as an amphoteric, anionic, cationic or nonionic emulsifier, used alone or as a mixture, and optionally a co-emulsifier. The emulsifiers are chosen in an appropriate manner according to the emulsion to be obtained (W/O or O/W). The emulsifier and the co-emulsifier are generally present in the composition in a proportion ranging from 0.3% to 30% by weight and preferably from 0.5% to 20% by weight relative to the total weight of the composition.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt. A crosslinked elastomeric solid organopolysiloxane comprising at least one oxyalkylene group, such as those obtained according to the procedure of Examples 3, 4 and 8 of U.S. Pat. No. 5,412,004 and of the examples of U.S. Pat. No. 5,811,487, especially the product of Example 3 (synthesis example) of U.S. Pat. No. 5,412,004, such as the product sold under the reference KSG 21 by the company Shin-Etsu, may also be used as surfactants for W/O emulsions.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The fatty acid esters of a sugar that can be used as nonionic amphiphilic lipids can be chosen in particular from the group comprising esters or mixtures of esters of a $C_8$-$C_{22}$ fatty acid and of sucrose, of maltose, of glucose or of fructose, and esters or mixtures of esters of a $C_{14}$-$C_{22}$ fatty acid and of methylglucose.

The $C_8$-$C_{22}$ or $C_{14}$-$C_{22}$ fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearte, sucrose distearate, sucrose tristearate and mixtures thereof, such as the products sold by the company Croda under the name Crodesta™ F50, F70, F110 and F160 having, respectively, an HLB (Hydrophilic Lipophilic Balance) of 5, 7, 11 and 16; and, by way of example of esters or of mixtures of esters of a fatty acid and of methylglucose, mention may be made of the disearate of methylglucose and of polyglycerol-3, sold by the company Goldschmidt under the name Tego® Care 450. Mention may also be made of glucose monoesters or maltose monoesters, such as methyl O-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a $C_8$-$C_{22}$ fatty alcohol and of glucose, of maltose, of sucrose or of fructose, and ethers or mixtures of ethers of a $C_{14}$-$C_{22}$ fatty alcohol and of methylglucose. They are in particular alkylpolyglucosides.

The $C_8$-$C_{22}$ or $C_{14}$-$C_{22}$ fatty alcohols forming the fatty unit of the ethers that can be used in the emulsion of the instant disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglucoside and laurylglucoside sold, for example, by the company Henkel under the respective names Plantaren® 2000 and Plantaren® 1200, cetostearylglucoside, optionally as a mixture with cetostearyl alcohol, sold, for example, under the name Montanov™ 68 by the company Seppic, under the name Tego® Care CG90 by the company Goldschmidt and under the name Emulgade® KE3302 by the company Henkel, and also arachidylglucoside, for example in the form of the mixture of arachidyl and behenyl alcohols and of arachidylglucoside sold under the name Montanov™ 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The glycerol fatty esters that can be used as nonionic amphiphilic lipids can be chosen in particular from the group comprising the esters formed from at least one acid comprising a saturated linear alkyl chain having from 16 to 22 carbon atoms, and from 1 to 10 glycerol units. Use may be made of one or more of these glycerol fatty esters in the emulsion of the instant disclosure.

These esters may be chosen in particular from stearates, behenates, arachidates, palmitates and mixtures thereof. Stearates and palmitates are preferably used.

By way of example of a surfactant that can be used in the emulsion of the instant disclosure, mention may be made of decaglycerol monostearate, distearate, tristearate and pentastearate (10 glycerol units) (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1-S, 2-S, 3-S and 5-S by the company Nikko, and diglyceryl monostearate (CTFA name: polyglyceryl-2 stearate) such as the product sold by the company Nikko under the name Nikkol DGMS.

The sorbitan fatty esters that can be used as nonionic amphiphilic lipids chosen in particular from the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid comprising at least one saturated linear alkyl chain, having, respectively, from 16 to 22 carbon atoms, and from sorbitol or from ethoxylated sorbitol. The oxyethylenated esters generally comprise from 1 to 100 ethylene oxide units, and preferably from 2 to 40 ethylene oxide (EO) units.

These esters can be chosen in particular from stearates, behenates, arachidates, palmitates and mixtures thereof. Stearates and palmitates are preferably used.

By way of example of sorbitan fatty ester and of an oxyethylenated sorbitan fatty ester, mention may be made of sorbitan monostearate (CTFA name: sorbitan stearate) sold by the company ICI under the name Span® 60, sorbitan monopalmitate (CTFA name: sorbitan palmitate) sold by the company ICI under the name Span® 40, or sorbitan 20 EO tristearate (CTFA name: polysorbate 65) sold by the company ICI under the name Tween® 65.

The ethoxylated fatty ethers are typically ethers made up of 1 to 100 ethylene oxide units and of at least one fatty alcohol chain having from 16 to 22 carbon atoms. The fatty chain of the ethers can be chosen in particular from behenyl, arachidyl, stearyl and cetyl units, and mixtures thereof, such as cetearyl. By way of example of ethoxylated fatty ethers, mention may be made of ethers of behenyl alcohol comprising 5, 10, 20 and 30 ethylene oxide units (CTFA names: beheneth-5, beheneth-10, beheneth-20 and beheneth-30), such as the products sold under the names Nikkol BB5, BB10, BB20 and BB30 by the company Nikko, and the ether of stearyl alcohol comprising 2 ethylene oxide units (CTFA name: steareth-2), such as the product sold under the name Brij™ 72 by the company ICI.

The ethoxylated fatty esters that can be used as nonionic amphiphilic lipids are esters made up of 1 to 100 ethylene oxide units and of at least one fatty acid chain comprising from 16 to 22 carbon atoms. The fatty chain of the esters can be chosen in particular from stearate, behenate, arachidate and palmitate units, and mixtures thereof. By way of example of ethoxylated fatty esters, mention may be made of the ester of stearic acid comprising 40 ethylene oxide units, such as the product sold under the name Myrj 52 (CTFA name: PEG-40 stearate) by the company ICI, and the ester of behenic acid comprising 8 ethylene oxide units (CTFA name: PEG-8 behenate), such as the product sold under the name Compritol® HD5 ATO by the company Gattefosse.

The block copolymers of ethylene oxide and of propylene oxide that can be used as nonionic amphiphilic can be chosen in particular from poloxamers and in particular from Poloxamer 231, such as the product sold by the company ICI under the name Pluronic® L81 of formula (V) with x=z=6, y=39 (HLB 2); Poloxamer 282, such as the product sold by the company ICI under the name Pluronic®L92 of formula (V) with x=z=10, y=47 (HLB 6); and Poloxamer 124, such as the product sold by the company ICI under the name Pluronic® L44 of formula (V) with x=z=11, y=21 (HLB 16).

As nonionic amphiphilic lipids, mention may also be made of the mixtures of nonionic surfactants described in document EP-A-705593, incorporated herein for reference.

Suitable hydrophobically-modified emulsifiers include, for example, inulin lauryl carbamate, commercially available from Beneo Orafti under the tradename Inutec SP1.

The above lists are only examples and not limiting.

The total amount of emulsifier present in the compositions is typically in an amount of about 0.1, 0.2, or 0.5 wt. % to about 4.0, 5.0, 6.0, 7.0, 8.0, 9.0, or 10.0 wt. %, based on the total weight of the composition.

Sunscreen Actives

The organic UV-screening agents are chosen especially from cinnamic derivatives; anthranilates; salicylic derivatives; dibenzoylmethane derivatives; camphor derivatives; benzophenone derivatives; β,β-diphenylacrylate derivatives; triazine derivatives; benzotriazole derivatives; benzalmalonate derivatives, especially those cited in patent U.S. Pat. No. 5,624,663; benzimidazole derivatives; imidazolines; bis-benzoazolyl derivatives as described in patents EP669323 and U.S. Pat. No. 2,463,264; p-aminobenzoic acid (PABA) derivatives; methylene bis(hydroxyphenylbenzotriazole) derivatives as described in applications U.S. Pat. No. 5,237,071, U.S. Pat. No. 5,166,355, GB2303549, DE19726184 and EP893119; benzoxazole derivatives as described in patent applications EP0832642, EP1027883, EP1300137 and DE10162844; screening polymers and screening silicones such as those described especially in patent application WO 93/04665; dimers derived from α-alkylstyrene such as those described in patent application DE 19855649; 4,4-diarylbutadienes such as those described in patent applications EP0967200, DE19746654, DE19755649, EP-A-1008586, EP1133980 and EP1133981, merocyanine derivatives such as those described in patent applications WO 04/006878, WO 05/058269 and WO 06/032741; and mixtures thereof.

As examples of complementary organic photoprotective agents, mention may be made of those denoted hereinbelow under their INCI name:

Cinnamic Derivatives:

Ethylhexyl Methoxycinnamate sold in particular under the trade name "Parsol® MCX" by DSM Nutritional Products, Isopropyl Methoxycinnamate, Isoamyl Methoxycinnamate sold under the trade name "Neo Heliopan® E 1000" by Symrise, DEA Methoxycinnamate, Diisopropyl Methylcinnamate, Glyceryl Ethylhexanoate Dimethoxycinnamate.

Dibenzoylmethane Derivatives:

Butyl Methoxydibenzoylmethane sold especially under the trade name "Parsol® 1789" by DSM, Isopropyl Dibenzoylmethane.

Para-Aminobenzoic Acid Derivatives:

PABA, Ethyl PABA, Ethyl Dihydroxypropyl PABA, Ethylhexyl dimethyl PABA sold in particular under the name "Escalol™ 507" by ISP, Glyceryl PABA, PEG-25 PABA sold under the name "Uvinul® P25" by BASF.

Salicylic Derivatives:

Homosalate sold under the name "Eusolex® HMS" by Rona/EM Industries, Ethylhexyl Salicylate sold under the name "Neo Heliopan® OS" by Symrise, Dipropylene Glycol Salicylate sold under the name "Dipsal™" by Scher, TEA Salicylate sold under the name "Neo Heliopan® TS" by Symrise.

β,β-Diphenylacrylate Derivatives:

Octocrylene sold in particular under the trade name "Uvinul® N539" by BASF, Etocrylene sold in particular under the trade name "Uvinul® N35" by BASF.

Benzophenone Derivatives:

Benzophenone-1 sold under the trade name "Uvinul® 400" by BASF, Benzophenone-2 sold under the trade name "Uvinul® D50" by BASF, Benzophenone-3 or Oxybenzone sold under the trade name "Uvinul® M40" by BASF, Benzophenone-4 sold under the trade name "Uvinul® MS40" by BASF, Benzophenone-5, Benzophenone-6 sold under the trade name "Helisorb® 11" by Norquay, Benzophenone-8 sold under the trade name "Spectra-Sorb UV-24" by American Cyanamid, Benzophenone-9 sold under the trade name "Uvinul® DS-49" by BASF, Benzophenone-12, n-Hexyl 2-(4-diethylamino-2-hydroxybenzoyl)benzoate sold under the trade name "Uvinul® A+" or as a mixture with octyl methoxycinnamate under the trade name "Uvinul® A+B" by BASF.

Benzylidenecamphor Derivatives:

3-Benzylidene Camphor manufactured under the name "Mexoryl™ SD" by Chimex, 4-Methylbenzylidene Camphor sold under the name "Eusolex® 6300" by Merck, Benzylidene Camphor Sulfonic Acid manufactured under the name "Mexoryl™ SL" by Chimex, Camphor Benzalkonium Methosulfate manufactured under the name "Mexoryl™ SO" by Chimex, Terephthalylidene Dicamphor Sulfonic Acid manufactured under the name "Mexoryl™ SX" by Chimex, Polyacrylamidomethyl Benzylidene Camphor manufactured under the name "Mexoryl™ SW" by Chimex.

Phenylbenzimidazole Derivatives:

Phenylbenzimidazole Sulfonic Acid sold in particular under the trade name "Eusolex® 232" by Merck, Disodium Phenyl Dibenzimidazole Tetrasulfonate sold under the trade name "Neo Heliopan® AP" by Symrise.

Phenylbenzotriazole Derivatives:

Drometrizole Trisiloxane sold under the name "Silatrizole" by Rhodia Chimie, Methylene bis-Benzotriazolyl Tetramethylbutyl-phenol sold in solid form under the trade name "MIXXIM BB/100" by Fairmount Chemical, or in micronized form as an aqueous dispersion under the trade name "Tinosorb M" by Ciba Specialty Chemicals.

Triazine Derivatives:

bis-Ethylhexyloxyphenol Methoxyphenyl Triazine sold under the trade name "Tinosorb® S" by BASF, Ethylhexyl Triazone sold in particular under the trade name "Uvinul® T150" by BASF, Diethylhexyl Butamido Triazone sold under the trade name "Uvasorb® HEB" by Sigma 3V, 2,4,6-tris(dineopentyl 4'-aminobenzalmalonate)s-triazine, 2,4,6-tris(diisobutyl 4'-aminobenzalmalonate)s-triazine, 2,4-bis(dineopentyl 4'-aminobenzalmalonate)-6-(n-butyl 4'-aminobenzoate)-s-triazine, symmetrical triazine screening agents described in patent U.S. Pat. No. 6,225,467, patent application WO 2004/085412 (see compounds 6 and 9) or the document "Symmetrical Triazine Derivatives" IP.COM Journal, IP.COM Inc., West Henrietta, N.Y., US (20 Sep. 2004), especially 2,4,6-tris(biphenyl)-1,3,5-triazines (in particular 2,4,6-tris(biphenyl-4-yl)-1,3,5-triazine and 2,4,6-tris(terphenyl)-1,3,5-triazine, which is included in patent applications WO 06/035000, WO 06/034982, WO 06/034991, WO 06/035007, WO 2006/034992 and WO 2006/034985).

Anthranilic Derivatives:

Menthyl Anthranilate sold under the trade name "Neo Heliopan® MA" by Symrise.

Imidazoline Derivatives:

Ethylhexyl Dimethoxybenzylidene Dioxoimidazoline Propionate.

Benzalmalonate Derivatives:

Polyorganosiloxane containing benzalmalonate functions, for instance Polysilicone-15, sold under the trade name "Parsol® SLX" by DSM Nutritional Products.

4,4-Diarylbutadiene Derivatives:

1,1-dicarboxy(2,2'-dimethylpropyl)-4,4-diphenylbutadiene.

Benzoxazole Derivatives:

2,4-bis[5-(1-dimethylpropyl)benzoxazol-2-yl-(4-phenyl)imino]-6-(2-ethylhexyl)imino-1,3,5-triazine sold under the name Uvasorb® K2A by Sigma 3V, and mixtures thereof.

The Preferential Organic Screening Agents are Chosen from:

Ethylhexyl Methoxycinnamate, Ethylhexyl Salicylate, Homosalate, Butyl Methoxydibenzoylmethane, Octocrylene, Phenylbenzimidazole Sulfonic Acid, Benzophenone-3, Benzophenone-4, Benzophenone-5, n-Hexyl 2-(4-diethylamino-2-hydroxybenzoyl)benzoate, 4-Methylbenzylidene Camphor, Terephthalylidene Dicamphor Sulfonic Acid, Disodium Phenyl Dibenzimidazole Tetrasulfonate, Methylene Bis-Benzotriazolyl Tetramethylbutylphenol, Bis-Ethylhexyloxyphenol Methoxyphenyl Triazine, Ethylhexyl triazone, Diethylhexyl Butamido Triazone, 2,4,6-Tris(dineopentyl 4'-aminobenzalmalonate)-s-triazine, 2,4,6-Tris(diisobutyl 4'-aminobenzalmalonate)-s-triazine, 2,4-Bis(dineopentyl 4'-aminobenzalmalonate)-6-(n-butyl 4'-aminobenzoate)-s-triazine, 2,4,6-Tris(biphenyl-4-yl)-1,3,5-triazine, 2,4,6-Tris(terphenyl)-1,3,5-triazine, Drometrizole Trisiloxane, Polysilicone-15, 1,1-dicarboxy(2,2'-dimethylpropyl)-4,4-diphenylbutadiene, 2,4-bis[5-1(dimethylpropyl)benzoxazol-2-yl-(4-phenyl)imino]-6-(2-ethylhexyl)imino-1,3,5-triazine, and mixtures thereof.

The inorganic UV screening agents used in accordance with the present invention are metal oxide pigments. More preferentially the inorganic UV screening agents of the invention are metal oxide particles having a mean elementary particle size of less than or equal to 500 nm, more preferably of between 5 nm and 500 nm and more preferably still of between 10 nm and 100 nm, and preferably between 15 nm and 50 nm.

They may be selected especially from titanium oxides, zinc oxides, iron oxides, zirconium oxides, cerium oxides or mixtures thereof.

Such coated or uncoated metal oxide pigments are described in particular in the patent application EP-A-0 518 773. Commercial pigments that may be mentioned include the products sold by the companies Kemira, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or of aluminium), polyethylene, silicones, proteins (collagen, elastin), alkanolamines, silicon oxides, metal oxides or sodium hexametaphosphate.

The coated pigments are more particularly titanium oxides that have been coated: with silica, such as the product "Sunveil" from the company Ikeda, with silica and iron oxide, such as the product "Sunveil F" from the company Ikeda, with silica and alumina, such as the products "Microtitanium Dioxide MT 500 SA" and "Microtitanium Dioxide MT 100 SA" from the company Tayca and "Tioveil™" from the company Tioxide, with alumina, such as the products "Tipaque TTO-55 (B)" and "Tipaque TTO-55 (A)" from the company Ishihara and "UVT 14/4" from the company Kemira, with alumina and aluminium stearate, such as the products "Microtitanium Dioxide MT 100 T, MT 100 TX, MT 100 Z and MT-01" from the company Tayca, the products "Solaveil™ CT-10 W" and "Solaveil™ CT 100", from the company Uniqema and the product "Eusolex® T-AVO" from the company Merck, with silica, alumina and alginic acid, such as the product "MT-100 AQ" from the company Tayca, with alumina and aluminium laurate, such as the product "Microtitanium Dioxide MT 100 S" from the company Tayca, with iron oxide and iron stearate, such as the product "Microtitanium Dioxide MT 100 F" from the company Tayca, with zinc oxide and zinc stearate, such as the product "BR 351" from the company Tayca, with silica and alumina and treated with a silicone, such as the products "Microtitanium Dioxide MT 600 SAS", "Microtitanium Dioxide MT 500 SAS" or "Microtitanium Dioxide MT 100 SAS" from the company Tayca, with silica, alumina and aluminium stearate and treated with a silicone, such as the product "STT-30-DS" from the company Titan Kogyo, with silica and treated with a silicone, such as the product "UV-Titan X 195" from the company Kemira, with alumina and treated with a silicone, such as the products "Tipaque TTO-55 (S)" from the company Ishihara or "UV Titan M 262" from the company Kemira, with triethanolamine, such as the product "STT-65-S" from the company Titan Kogyo, with stearic acid, such as the product "Tipaque TTO-55 (C)" from the company Ishihara, with sodium hexametaphosphate, such as the product "Microtitanium Dioxide MT 150 W" from the company Tayca.

$TiO_2$ treated with octyltrimethylsilane sold under the trade name "T 805" by the company Degussa Silices, $TiO_2$ treated with a polydimethylsiloxane sold under the trade name "70250 Cardre UF TiO2SI3" by the company Cardre, anatase/rutile $TiO_2$ treated with a polydimethylhydrogenosiloxane sold under the trade name "Microtitanium Dioxide USP Grade Hydrophobic" by the company Color Techniques.

The uncoated titanium oxide pigments are sold, for example, by the company Tayca under the trade names "Microtitanium Dioxide MT 500 B" or "Microtitanium Dioxide MT 600 B", by the company Degussa under the name "P 25", by the company Wackher under the name "Transparent titanium oxide PW", by the company Miyoshi Kasei under the name "UFTR", by the company Tomen under the name "ITS" and by the company Tioxide under the name "Tioveil™ AQ".

The uncoated zinc oxide pigments are, for example: those sold under the name "Z-Cote®" by the company Sunsmart; those sold under the name "Nanox®" by the company Elementis; those sold under the name "Nanogard™ WCD 2025" by the company Nanophase Technologies.

The coated zinc oxide pigments are, for example: those sold under the name "Zinc Oxide CS-5" by the company Toshibi (ZnO coated with polymethylhydrogensiloxane); those sold under the name "Nanogard™ Zinc Oxide FN" by the company Nanophase Technologies (as a 40% dispersion in Finsolva Tenn., $C_{12}$-$C_{14}$ alkyl benzoate); those sold under the name "Daitopersion Zn-30" and "Daitopersion Zn-50" by the company Daito (dispersions in cyclopolymethylsiloxane/oxyethylenated polydimethylsiloxane, containing 30% or 50% of nanozinc oxides coated with silica and polymethylhydrogensiloxane); those sold under the name "NFD Ultrafine ZnO" by the company Daikin (ZnO coated with perfluoroalkyl phosphate and copolymer based on perfluoroalkylethyl as a dispersion in cyclopentasiloxane); those sold under the name "SPD-Z1" by the company Shin-Etsu (ZnO coated with silicone-grafted acrylic polymer, dispersed in cyclodimethylsiloxane); those sold under the name "Escalol™ Z100" by the company ISP (alumina-treated ZnO dispersed in an ethylhexyl methoxycinnamate/PVP-hexadecene copolymer/methicone mixture); those sold under the name "Fuji ZnO-SMS-10" by the company Fuji Pigment (ZnO coated with silica and polymethylsilsesquioxane); those sold under the name "Nanox® Gel TN" by the company Elementis (ZnO dispersed at a concentration of 55% in $C_{12}$-$C_{15}$ alkyl benzoate with hydroxystearic acid polycondensate).

The uncoated cerium oxide pigments may be for example those sold under the name "Colloidal Cerium Oxide" by the company Rhone-Poulenc.

The uncoated iron oxide pigments are sold, for example, by the company Arnaud under the names "Nanogard™ WCD 2002 (FE 45B)", "Nanogard™ Iron FE 45 BL AQ", "Nanogard™ FE 45R AQ" and "Nanogard™ WCD 2006 (FE 45R)" or by the company Mitsubishi under the name "TY-220".

The coated iron oxide pigments are sold, for example, by the company Arnaud under the names "Nanogard™ WCD 2008 (FE 45B FN)", "Nanogard™ WCD 2009 (FE 45B 556)", "Nanogard™ FE 45 BL 345" and "Nanogard™ FE 45 BL" or by the company BASF under the name "Transparent Iron Oxide".

Mention may also be made of mixtures of metal oxides, especially of titanium dioxide and of cerium dioxide, including the silica-coated equal-weight mixture of titanium dioxide and of cerium dioxide, sold by the company Ikeda under the name "Sunveil A", and also the alumina-, silica- and silicone-coated mixture of titanium dioxide and of zinc dioxide, such as the product "M 261" sold by the company Kemira, or the alumina-, silica- and glycerol-coated mixture of titanium dioxide and of zinc dioxide, such as the product "M 211" sold by the company Kemira.

According to the invention, coated or uncoated titanium oxide pigments are particularly preferred.

The sunscreen actives according to the invention are preferably present in the compositions according to the invention in a content ranging from about 0.1% to 40% by weight and in particular from 5% to 35% by weight, relative to the total weight of the composition.

The compositions according to the invention may be used, for example, as a care product and/or sun protection product for the face and/or body having a liquid to semi-liquid consistency, such as milks, more or less rich creams, cream gels or pastes. They may optionally be packaged as an aerosol and may be in the form of a mousse or a spray.

The compositions according to the invention in the form of vaporizable lotions in accordance with the invention are applied to the skin or the hair in the form of fine particles by means of pressurization devices. The devices in accordance with the invention are well known to those skilled in the art and comprise non-aerosol pumps or "atomizers", the aerosol containers comprising a propellant, and also aerosol pumps using compressed air as propellant. These pumps are described in patents U.S. Pat. No. 4,077,441 and U.S. Pat. No. 4,850,517 (which form an integral part of the content of the description).

The compositions packaged in aerosol form in accordance with the invention generally contain conventional propellants, for instance hydrofluoro compounds, dichloro-difluoromethane, difluoroethane, dimethyl ether, isobutane, n-butane, propane or trichlorofluoromethane. They are preferably present in amounts ranging from 15% to 50% by weight relative to the total weight of the composition.

The following examples serve to illustrate the invention without however exhibiting a limiting character. In these examples the amounts of the composition ingredients are given as weight percentages relative to the total weight of the composition.

Examples

TABLE 1

Inventive Examples

| Ingredients | Ex. 1 | Ex. 2 | Ex. 3 | Ex. 4 | Ex. 5 |
|---|---|---|---|---|---|
| Phase A | | | | | |
| DEMINERALIZED WATER | QS 100 | QS 100 | QS 100 | QS 100 | QS 100 |
| ACRYLATES/C10-30 ALKYL ACRYLATE CROSSPOLYMER | 0.15 | 0.15 | 0.15 | 0.15 | 0.15 |
| SODIUM POLYACRYLATE | 1 | 0.4 | 0.4 | 0.4 | 0.4 |
| CHELATING AGENT | 0.1 | 0.1 | 0.1 | 0.1 | 0.1 |
| PRESERVATIVES | 0.7 | 0.7 | 0.7 | 0.7 | 0.7 |
| Phase B | | | | | |
| UV FILTERS | 20 | 27.29 | 20 | 20 | 20 |
| CAPRYLYL GLYCOL | 0.5 | 0.5 | 0.5 | 0.5 | 0.5 |
| ANTI-OXIDANTS | 0.1 | 0.2 | 0.1 | 0.2 | 0.2 |
| Phase B1 | | | | | |
| STYRENE/ACRYLATES COPOLYMER | 1 | | | | |
| Phase C | | | | | |
| DIMETHICONE | 3 | 3 | 3 | 3 | 3 |
| ACRYLATES/DIMETHICONE COPOLYMER | 0.305 | 0.915 | 0.915 | 0.915 | 0.915 |
| Phase D | | | | | |
| SILICA | 1 | 1 | 1 | 0.25 | 0.25 |
| Phase E | | | | | |
| pH ADJUSTERS | | | | | |
| Phase F | | | | | |
| ALCOHOL DENAT. | 10 | 10 | 10 | 10 | 5 |

TABLE 2

Comparative Examples

| Ingredients | Ex. 6 | Ex. 7 | Ex. 8 | Ex. 9 |
|---|---|---|---|---|
| Phase A | | | | |
| DEMINERALIZED WATER | QS 100 | QS 100 | QS 100 | QS 100 |
| ACRYLATES/C10-30 ALKYL ACRYLATE CROSSPOLYMER | 0.15 | 0.15 | 0.15 | |
| SODIUM POLYACRYLATE | | 0.4 | 0.9 | |
| CHELATING AGENT | 0.1 | 0.1 | 0.1 | 0.1 |
| PRESERVATIVES | 0.7 | 0.7 | 0.7 | 0.5 |
| INULIN LAURYL CARBAMATE | | | | 0.29 |
| HYDROXYETHYLCELLULOSE | | | | 0.1 |
| GLYCERIN | | | | 5 |
| Phase B | | | | |
| UV FILTERS | 20 | 20 | 20 | 20 |
| CAPRYLYL GLYCOL | 0.5 | 0.5 | 0.5 | |
| ANTI-OXIDANTS | 0.2 | 0.2 | 0.2 | |
| ETHYLENEDIAMINE/STEARYL DIMER DILINOLEATE COPOLYMER | | | 3.99 | |
| DIMETHICONE (and) DIMETHICONOL | | | | 1 |
| POLYSILICONE-11 | | | | 3.25 |
| BIS-PEG/PPG-16/16 PEG/PPG-16/16 DIMETHICONE (and) CAPRYLIC/CAPRIC TRIGLYCERIDE (87/13) | | | | 2 |
| Phase C | | | | |
| DIMETHICONE | 3 | 3 | 3 | |
| ACRYLATES/DIMETHICONE COPOLYMER | | | 0.915 | |
| Phase D | | | | |
| SILICA | 1 | 1 | 1 | 3 |
| AMMONIUM POLYACRYLOYLDIMETHYL TAURATE | | | | 0.88 |
| PERLITE | | 1 | | |
| Phase E | | | | |
| pH ADJUSTERS | | | 0.12 | |
| Observation after 12 weeks at RT | Not Stable | Not Stable | Not Stable | Not Stable |

In making each of the examples in Tables 1 and 2, the following procedure was used.

The ingredients of Phase A (aqueous phase) were combined in the main kettle, heated to 40-45° C. with propeller mixing, and mixed until homogeneous. The ingredients of phase B (oil phase) were combined in a side kettle, heated to 50° C., and mixed until homogeneous. The contents of the side kettle were added to the main kettle and mixed with a propeller for 20 minutes. The contents of the main kettle were cooled to RT. At 40° C., phases C and D were added and mixed until homogeneous. Phase E was pre-mixed and added to the main kettle at RT. The contents of the main kettle were mixed until homogeneous. The contents of the main kettle were mixed until homogeneous.

This is Table 3. In-vivo Water Resistance Test

| Formula | SPF (Static) | SPF (Water Resistant) | Percent Retention |
|---|---|---|---|
| Example 5 (Inventive Composition) | 39.20 | 36.58 | 93.3% |

SPF was determined under static and water resistant conditions (80 minutes) on human skin as defined by the FDA Sunscreen Final Rule; under 21 CFR Parts 201 and 301, Labeling and Effectiveness Testing; Sunscreen Drug Products for Over-the-Counter Human Use, publication date Jun. 17, 2011. Samples were tested on 10 subjects.

This is Table 4. In-vitro Transparency on Wet Skin

| Test Product | Technology | Observations |
| --- | --- | --- |
| Example 4 (Inventive Composition) | Gel Suspension | No signs of whitening |
| Example 6 (Comparative Composition) | Gel Suspension | Slight white streaks |
| Example 7 (Comparative Composition) | Gel Suspension | Minimal white streaks |
| Example 8 (Comparative Composition) | Gel Suspension | White |
| Banana Boat SPF 30 Sport Lotion (Comparative Composition) | O/W Nonionic Emulsion | Streaky and white appearance |
| Banana Boat SPF 50 Sport Lotion (Comparative Composition) | O/W Nonionic Emulsion | Streaky and white appearance |
| Coppertone Sport Lotion SPF 50 (Comparative Composition) | O/W Nonionic Emulsion | Streaky and white appearance |
| Neutrogena Ultra Sheer Dry Touch SPF 55 (Comparative Composition) | O/W Nonionic Emulsion | Streaky and white appearance |

Deionized water (2 mg/cm$^2$) was applied to the inside forearm of a subject. Test product (2 mg/cm$^2$) was applied to the same area and rubbed in. Sample's color, spreadability, and integrity were evaluated visually during rub-in. Forearm was placed under running water to determine if product washed off. The results demonstrate that the inventive composition exhibits no signs of whitening upon application to wet skin while the comparative compositions are white and streaky upon application to wet skin.

This is Table 5. In-vitro Film Integrity Test on Wet Skin

| Test Product | Technology | Observations |
| --- | --- | --- |
| Example 4 (Inventive Composition) | Gel Suspension | Uniform color and intensity. Even film |
| Example 6 (Comparative Composition) | Gel Suspension | Minimal blotchiness |
| Example 7 (Comparative Composition) | Gel Suspension | Some blotchiness |
| Example 8 (Comparative Composition) | Gel Suspension | Uneven film with streaks |
| Banana Boat SPF 30 Sport Lotion (Comparative Composition) | O/W Nonionic Emulsion | Uneven film with streaks |
| Banana Boat SPF 50 Sport Lotion (Comparative Composition) | O/W Nonionic Emulsion | Uneven film with streaks |
| Coppertone Sport Lotion SPF 50 (Comparative Composition) | O/W Nonionic Emulsion | Uneven film with streaks |
| Neutrogena Wet Skin Lotion SPF 45 (Comparative Composition) | O/W Nonionic Emulsion | Uneven film with streaks |
| Neutrogena Ultra Sheer Dry Touch SPF 55 (Comparative Composition) | O/W Nonionic Emulsion | Uneven film with streaks |

Deionized water (0.1 mL) was applied to a 5 cm×5 cm area on the inside forearm of a subject and rubbed for 10 seconds. Test product (0.02 mL) was applied to the same 5 cm×5 cm area and rubbed for 10 seconds. The test site was illuminated under a Wood's lamp and evaluated visually. Under a Wood's lamp, the product has a fluorescent purple color. Streaks and uneven film can be detected by different shades/intensities of purple color in the test area.

The results demonstrate that the inventive composition forms an even film upon application to wet skin while the comparative composition does not form a uniform film upon application to wet skin.

What is claimed is:

1. A composition consisting of:
   (a) an acrylates/C10-30 alkyl acrylate crosspolymer;
   (b) a neutralized polyacrylic acid selected from the group consisting of sodium, potassium, lithium and ammonium neutralized salts of polyacrylic acid;
   (c) a silicone acrylate selected from the group consisting of an acrylates/dimethicone copolymer and a graft copolymer having an acrylic acid polymer backbone and polydimethylsiloxane side chains;
   (d) an oil;
   (e) a sunscreen active;
   (f) an emulsifier;
   (g) one or more of a chelating agent, a preservative, a propellant, an anti-oxidant, silica, pH adjuster, and a monohydric C1-C8 alcohol; and
   (h) water,
   wherein the composition is initially clear in appearance and remains clear in appearance and does not result in one or more of a white appearance and white streaking upon application onto a wet keratinous substrate.

2. The composition of claim 1 wherein (a) is present in an amount of about 0.01 to 0.5% by weight, based on the total weight of the composition.

3. The composition of claim 1 wherein (a) is present in an amount of about 0.01 to 0.4% by weight, based on the total weight of the composition.

4. The composition of claim 1 wherein (b) is sodium polyacrylate.

5. The composition of claim 4 wherein (b) is present in an amount of about 0.01 to 0.5% by weight, based on the total weight of the composition.

6. The composition of claim 4 wherein (b) is present in an amount of about 0.01 to 1% by weight, based on the total weight of the composition.

7. The composition of claim 1 wherein (c) is an acrylates/dimethicone copolymer.

8. The composition of claim 7 wherein (c) is present in an amount of about 0.01 to 20% by weight, based on the total weight of the composition.

9. The composition of claim 7 wherein (c) is present in an amount of about 0.01 to 10% by weight, based on the total weight of the composition.

10. The composition of claim 1 wherein (d) is present in an amount of about 0.1 to 40% by weight, based on the total weight of the composition.

11. The composition of claim 1 wherein (d) is present in an amount of about 0.1 to 30% by weight, based on the total weight of the composition.

12. The composition of claim 1 wherein (e) is present in an amount of about 0.1 to 40% by weight, based on the total weight of the composition.

13. The composition of claim 1 wherein
   (a) the acrylates/C10-30 alkyl acrylate crosspolymer is present in an amount of about 0.01 to 0.5% by weight, based on the total weight of the composition, and
   (b) is sodium polyacrylate present in an amount of about 0.01 to 0.5% by weight, based on the total weight of the composition, and
   (c) is an acrylates/dimethicone copolymer present in an amount of about 0.01 to 20% by weight, based on the total weight of the composition, and (d) is present in an amount of about 0.1 to 40% by weight, based on the total weight of the composition, and
(e) is present in an amount of about 0.1 to 40% by weight, based on the total weight of the composition.

14. A composition consisting of:
(a) from about 0.01 to about 0.3% by weight of acrylates/C10-30 alkyl acrylate crosspolymer;
(b) from about 0.01 to about 0.75% by weight of sodium polyacrylate;
(c) from about 0.05 to about 5% by weight of acrylates/dimethicone copolymer;
(d) from about 0.1 to about 30% by weight of oil;
(e) from about 0.1 to about 40% by weight of sunscreen active;
(f) an emulsifier;
(g) one or more of a chelating agent, a preservative, a propellant, an anti-oxidant, silica, pH adjuster, and a monohydric C1-C8 alcohol; and
(h) water,
wherein the composition is initially clear in appearance and remains clear in appearance and does not result in one or more of a white appearance and white streaking upon application onto a wet keratinous substrate.

15. A method of protecting a keratinous substrate from UV rays comprising applying onto the keratinous substrate the clear composition according to claim 1.

\* \* \* \* \*